United States Patent [19]
Wilson

[11] Patent Number: 5,857,980
[45] Date of Patent: Jan. 12, 1999

[54] METHOD AND APPARATUS FOR DETECTING ONSET OF GASTRIC DYSRHYTHMIAS AND IMMINENT NAUSEA

[75] Inventor: Neil Wilson, Ephrata, Pa.

[73] Assignee: Beneva, Ltd., Ephrata, Pa.

[21] Appl. No.: 778,617

[22] Filed: Jan. 6, 1997

[51] Int. Cl.[6] ........................................ A61B 5/04
[52] U.S. Cl. ............................ 600/546; 600/593
[58] Field of Search ................... 600/546, 595, 600/593

[56] References Cited

U.S. PATENT DOCUMENTS

| | | | |
|---|---|---|---|
| 5,292,344 | 3/1994 | Douglas | 607/40 |
| 5,361,775 | 11/1994 | Remes et al. | 128/733 |
| 5,474,083 | 12/1995 | Church et al. | 128/733 |
| 5,659,136 | 8/1997 | Koch et al. | 73/462 |
| 5,690,691 | 11/1997 | Chen et al. | 607/40 |

*Primary Examiner*—Max Hindenburg
*Assistant Examiner*—Charles Marmor, III
*Attorney, Agent, or Firm*—Evenson, McKeown, Edewards & Lenahan, P.L.L.C.

[57] ABSTRACT

The invention provides a method and apparatus for automatically detecting loss of normal gastric myoelectrical activity and certain gastric dysrhythmias which indicate an imminent onset of nausea. Analog signals indicative of gastric myoelectrical activity are detected via electrodes, conditioned and then digitized. The resulting digital signals are passed through a digital band pass filter which has a pass band with a lower limit set at or near zero Hz, and the digitally conditioned signals are compared in a digital computer with stored predetermined signal patterns that are known to be indicative of the onset of imminent nausea. Upon detection of a match, an alarm is activated.

27 Claims, 2 Drawing Sheets

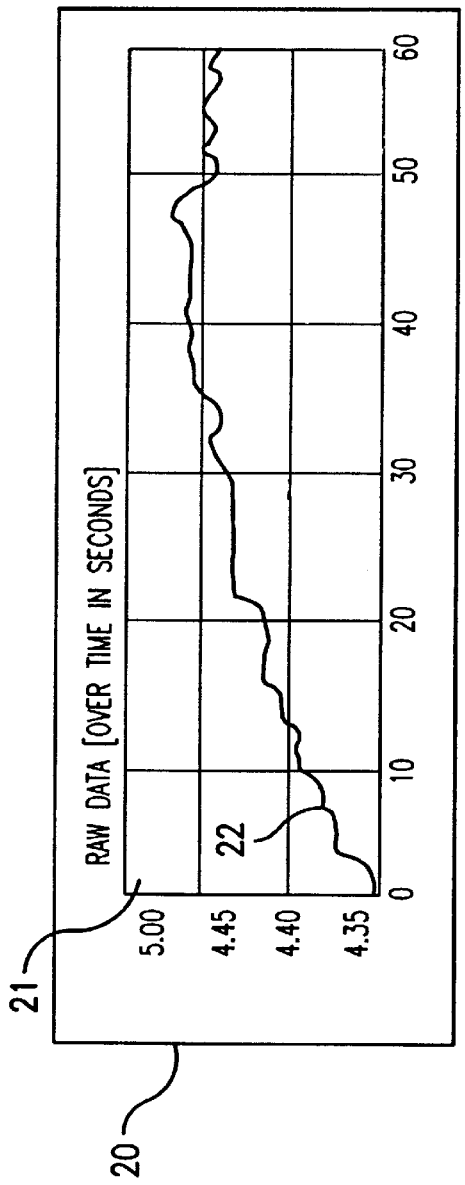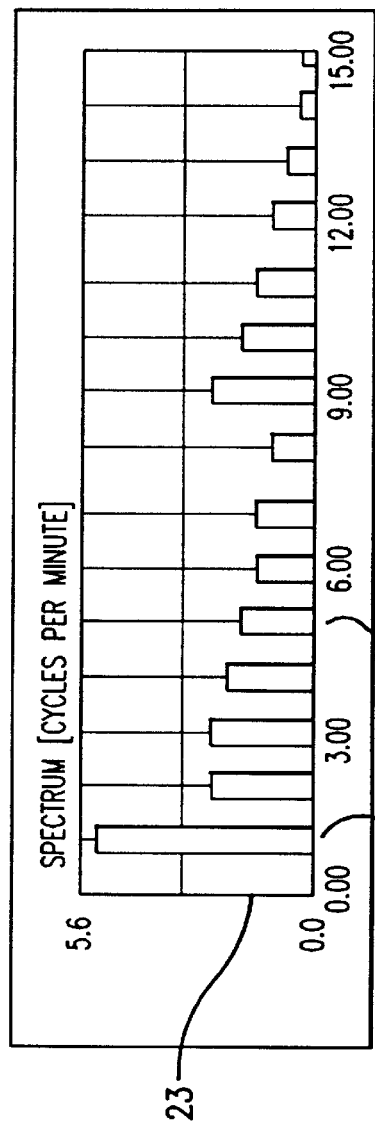

METHOD AND APPARATUS FOR DETECTING ONSET OF GASTRIC DYSRHYTHMIAS AND IMMINENT NAUSEA The present invention relates to a method and apparatus for automatically detecting and identifying the presence of certain physiological conditions which are indicative of the imminent onset of nausea in human beings. In particular, the invention relates to automatically detecting and identifying certain gastric dysrhythmias which precede the onset of nausea.

BACKGROUND OF THE INVENTION

Nausea, which is a noxious symptom that often leads to vomiting, is a problem frequently encountered in the field of medicine. Patients recovering from anesthesia, and those undergoing chemotherapy for cancer, for example, frequently become gravely nauseous.

Nausea can have serious implications aside from the extreme discomfort experienced by a patient or other individual who experiences it. In particular, nausea can be dangerous because the associated retching creates high pressures within the body that may cause hemorrhaging and disruption of sutures, especially in the eye and brain. In addition, vomiting can cause excessive loss of electrolytes as well as the possibility of aspiration in patients who are recovering from surgery or who are otherwise incapacitated.

It would thus be most useful in the field of medicine if a simple automated arrangement were available which reliably and timely predicts the onset of nausea. An objective physiological measure of impending nausea would be useful in managing patients with a wide variety of medical and surgical procedures. However, known prior art nausea detection techniques require constant observation and monitoring of the patient by a skilled individual.

Research has shown that gastric dysrhythmia (abnormal stomach electrical activity) heralds the onset of nausea induced during motion sickness and by the administration of the narcotic drug morphine sulfate. Gastric dysrhythmias are abnormal gastric myoelectrical rhythms termed tachygastrias (3.6–9.9 cycles per minute (cpm)) and bradygastrias (0–2.4 cpm) and are differentiated from normal gastric myoelectrical rhythms which occur within the range of 2.4 to 3.6 cpm.

Electrogastrograpy is a non-invasive method for recording gastric myoelectrical activity or electrogastrograms (EGGs) from normal rhythms to gastric dysrhythmias. Gastric dysrhythmias have been recorded with this method in patients with nausea of pregnancy, diabetic and idiopathic gastroparesis, and in patients with idiopathic nausea and drug-induced nausea. The onset of gastric dysrhythmias precedes the report of nausea by 1–20 minutes, depending on specific circumstances. The ability to recognize these gastric dysrhythmias automatically, in real time, would greatly improve the treatment of nausea at early stages and afford the physician an opportunity to prevent severe nausea, retching and vomiting.

The onset of gastric dysrhythmias and the loss of normal 2.4–3.6 cpm gastric rhythm may be identified by visual inspection of hard copy EGG records by a trained and specialized clinician or researcher who is skilled in the interpretation of gastric myoelectrical activity. Thus, known prior art devices are only able to record raw physiological EGG data and display it in real time, or provide spectral analyses off-line.

Real-time computer analysis, on the other hand, offers on-line quantitative analysis of gastric dysrhythmias. Thus, on-line reproduction of the gastric dysrhythmias and on-line quantitative and spectral analysis of the EGG signal would be important advances in the diagnosis and treatment of nausea.

Previous efforts to develop such a device, however, have been complicated by the fact that the electrical signals associated with stomach activity, and which are sensed for the purpose of analyzing gastric dysrhythmias, have a frequency which is extremely low, being on the order of a few cycles per minute (approximately 0.0–0.25 Hz) Thus far, efforts to develop an automated arrangement for analyzing electrical signals associated with stomach myoelectrical patterns have failed, due largely to the inability to eliminate artifacts (spurious signal components) in the signals. (That is, the signal to noise ratio is very low.) The existence of such artifacts has heretofore rendered any form of computer analysis unreliable.

SUMMARY OF THE INVENTION

Accordingly, it is an object of the present invention to provide a simple and reliable method and apparatus for accurately predicting the onset of nausea by automatically identifying loss of normal 2.4–3.6 cpm EGG activity and/or the presence of gastric dysrhythmias as described above.

Another object of the invention is to provide a method and apparatus which monitors and automatically analyzes gastric myoelectrical activity in real time or near real time, to detect and identify patterns associated with the imminent onset of nausea.

Still another object to the invention is to provide a method and apparatus for achieving an improved signal to noise ratio in an apparatus for automatically monitoring and analyzing myoelectrical activity.

A further object of the invention is to provide a method and apparatus for eliminating artifacts in low frequency electrical signals indicative of gastric myoelectrical activity.

Yet another object of the invention is to provide a method and apparatus for achieving an improved signal to noise ratio in the detection of extremely low frequency electrical signals.

These and other objects and advantages are achieved by the present invention, which provides near real time pattern recognition of low frequency physiological signals—between 0.00 and approximately 0.25 Hz. (Because of the need to sample such signals for at least a minute to obtain a reliable sample, the "near real time" analysis actually lags the signals themselves by one minute.) The gastric dysrhythmia/nausea detection apparatus according to the invention constructs a histogram showing the power distribution of such signals at various frequencies within the above frequency spectrum, and performs a pattern recognition to detect certain predetermined power levels and combinations of frequencies. In order to substantially eliminate artifacts in the low frequency signals and to facilitate accurate analysis thereof, a digital band pass filter is employed, with the lower limit of the pass band set at or very close to zero.

The gastric dysrhythmia/nausea monitor according to the invention is a portable computerized instrument which is connected to a human subject by means of standard EKG type electrodes attached to the epigastric area in the l vicinity of the stomach. The apparatus monitors and analyzes the stomach's myoelectrical activity in the form of analog electrical signals that are electronically detected through the abdominal wall. These signals are amplified, processed to remove electrical noise, unwanted electrical signals generated by physiological sources other than the stomach and external electrical interference from building facilities, machinery, etc. (analog signal conditioning), converted into digital form and processed by computer, in real time to improve further the quality of the signal (digital signal conditioning), to display the original signal and its spectrum and to analyze that signal for gastric dysrhythmias that are known to occur before the onset of nausea. The apparatus can produce audible and visual alarms when critical and quantitative values for gastric dysrhythmias are detected. It archives the digital form of the original signal derived from the subject, for on-the-spot historical review, for inclusion in the subject's medical dossier, or for later in-depth analysis, as desired.

In addition to activating an alarm when the detected pattern matches the shape or signature of a pattern that clinical research has identified as associated with impending nausea, the apparatus may also facilitate chemical intervention to alleviate nausea. In addition, a visual display of the histogram may be included, although such a display is not essential in view of the automated pattern recognition function of the invention.

Other objects, advantages and novel features of the present invention will become apparent from the following detailed description of the invention when considered in conjunction with the accompanying drawings.

BRIEF DESCRIPTION OF THE DRAWINGS

FIG. 2 shows a format for display of myoelectric data and a histogram representing a spectral power distribution associated therewith.

DETAILED DESCRIPTION OF THE DRAWINGS

Figure 1:
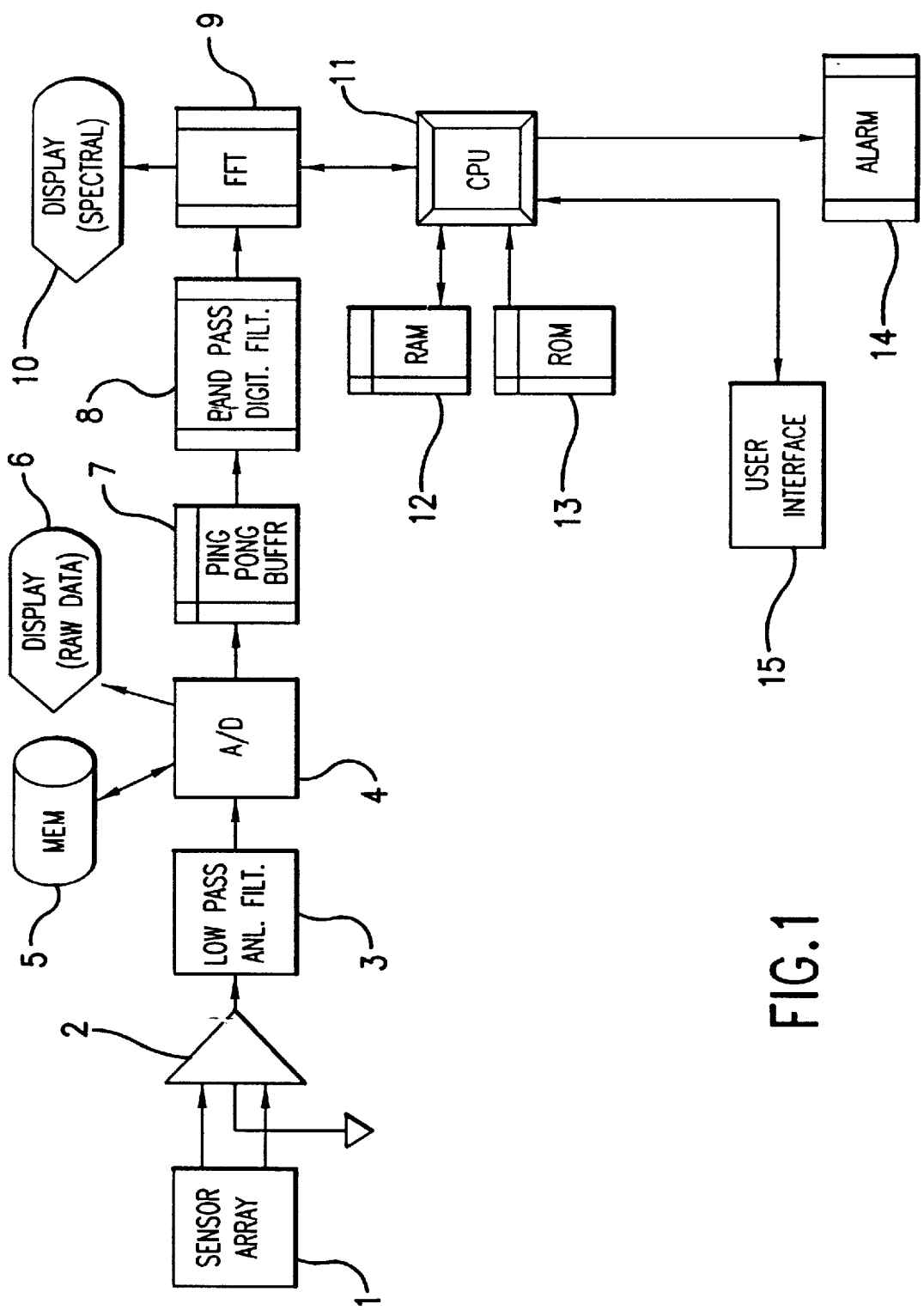
FIG. 1 is a conceptual block diagram which illustrates an arrangement for detecting the onset of gastric dysrhythmias in near real time according to the invention.

FIG. 1 of the drawing is a schematic depiction of a nausea monitoring and detection apparatus according to the invention. The sensor array 1 comprises a plurality of electrodes which are attached to the patient's skin in the area of the stomach. A variety of sensors are suitable for this purpose, including the type commonly used to detect myoelectrical activity for the purpose of recording electrocardiograms. Such sensors are well known to those skilled in the art, and conventionally are provided with adhesive backing which adheres to the patient's skin.

Analog electric signals from the sensor array 1, having a frequency in the range of 0.00—approximately 0.25 Hz, are amplified in a D.C. operational amplifier 2, which has an amplification factor of X1,000 to X10,000 for signals in the D.C. to 0.25 Hz range. The amplified signals are then passed through a conventional analog low pass filter, which may consist, for example, of a simple parallel capacitive network, and has an upper "roll off" limit of 0.25 Hz. (It is of course apparent that, depending on the circumstances, other higher or lower limits may be established.)

The filtered analog signals are then passed to the analog to digital converter 4, which samples and digitizes the analog signals at a sampling rate of 256 samples per minute. Numerous A/D converters are commercially available for this purpose, one example being National Instruments Model MIA-16X. The digitized signals are then stored in a hard disk memory 5, and may optionally be displayed on a monitor or other visual display 6. These signals are also entered into a buffer unit 7, which stores one minute of digitized data signals for processing by the CPU 11. Preferably the buffer unit is of the type commonly referred to as a "ping pong" buffer, which comprises two memory units, each of which has the capacity to store one minute of data, the contents of the two memory units being processed alternately. (That is, one memory unit collects data while data from the other is being processed.)

The digital data output from the buffer unit 7 is then passed through a band pass filter 8 having a lower limit which is set at zero Hz (in other words D.C.), and an upper limit set at 0.25 Hz. Numerous digital filters which are suitable for this purpose are known in the art of signal analysis. Two of the most advantageous types of filters are the Butterworth filter and the Chebyshev filter. The purpose of this step is to eliminate artifacts which tend to appear in the digitized signals above 15 cpm and at 1–2 cpm and lower, and have heretofore prevented reliable digital analysis. As discussed in more detail hereinbelow, it has been found that a band pass filter with a lower limit of the pass band set at or close to zero achieves results which are far superior to those attained with available conventional digital low pass filters.

The conditioned digital signals output by the band pass filter 8 are then processed in a Fast Fourier 5 Transformation (FFT) 9 to transform them from the time domain to the frequency domain. That is, FFT processing outputs a spectral analysis of the power distribution of the digitized conditioned myoelectrical signals, which can optionally be displayed on a display unit 10. In a preferred embodiment, the display of the frequency domain data in the display 10 and the time domain data in the display 6 may be combined in a single visual display unit, as shown in FIG. 2.

FIG. 2 is an example of a display format 20 for both time domain data (from the A/D converter 4) and the frequency domain information generated by the FFT process 9. It includes an upper portion 21 in which a moving sixty second window of the conditioned digitized data 22 is displayed. The lower portion 23 of the format 20 is a bar graph type presentation of the power distribution of the raw data signal 22 over a frequency of from zero to 15 cpm (0.00 to 0.25 Hz). As can be seen in the figure, the respective bars 24 represent the magnitude of signal 22 at each frequency from 0.00 to 15.00 cpm.

The information displayed in the histogram in the lower portion 23 of FIG. 2 can be used to detect myoelectrical signal patterns which are indicative of the onset of nausea. That is, clinical tests have shown that certain histogram patterns are extremely closely correlated with the onset of nausea within a time period 1 to 20 minutes thereafter. It is known, for example, that rapid shifts to, or a very small power component in, the 3.0 cpm range is indicative of imminent nausea, as is a large power component in the 9.0 cpm range. Combinations such as a small 3.0 cpm component and a large 9.0 cpm component can also be monitored to detect the onset of nausea.

As noted previously, the spectral distributions known to be associated with nausea can be monitored by having a skilled clinician continuously observe the display unit 10. Such an arrangement is obviously less efficient than a computerized arrangement, which automatically detects and identifies such patterns. However, as also noted, the presence of substantial artifacts in the 1–2 cpm range of the conditioned digitized myoelectrical signals has heretofore prevented accurate automated processing.

In the nausea monitoring arrangement according to the invention, histogram patterns which have been clinically determined to be reliable indicators of imminent nausea are stored in a memory unit such as ROM 13, together with conventional pattern recognition and signal processing and control software. A RAM 12 is also provided to store data which is currently being processed, as well as the results of such processing, software for operation of the device, and system software for controlling operation of the CPU 11.

The CPU 11 compares the input data from the FFT unit 9 with the predetermined problematic patterns stored in ROM 13 and when a match is determined to exist, an alarm 14 is activated. The alarm 14 may be any type of audio, visual or even tactile signalling unit. In addition, a user interface 15 is provided, by which the operator of the instrument may adjust the frequency patterns to be monitored, to reflect the circumstances of a particular patient, or other conditions which may affect the likelihood of nausea.

As noted previously, one of the difficulties associated with automated analysis of myoelectrical signals is their extremely low frequency spectrum. Little attention has been paid to the analysis of ultra low frequency (ULF) signals, especially physiological signals with frequencies lower than approximately 1.00 Hz. To study these frequencies, filtering is necessary to eliminate signals of higher frequencies. (The problems of "aliasing" and sub-harmonics are well known.) Methods currently used to filter, such as sampling, analog to digital converters, and Fourier transformations, do not eliminate artifacts.

One potential solution which has been used by researchers in the gastroenterology area, is low pass filtering. A low pass filter has only one (upper) limit above which all frequencies should be filtered. However, as noted previously, a low pass filter does not eliminate artifacts when the filter is used at very low frequencies.

A band pass filter, on the other hand, does substantially reduce or eliminate non-gastric, but phsyiological vs movement vs electronic artifacts when the lower limit is set at or close to zero and the upper limit is set to a value indicative of the upper limit of the frequency range that is of interest. It is important to note that it is unnecessary that the lower limit of the band pass filter be set exactly at zero in order to achieve satisfactory results in this regard. Rather it is sufficient if the lower limit is set at a value which is lower than the lowest frequency known to be of interest, which in this instance is approximately 1 cpm, a value which for practical purposes is very nearly zero. Using a band pass filter with the lower limit set at approximately zero in this manner achieves the desired elimination of artifacts, and at the same time assures that all relevant frequencies are taken into account.

It is not obvious to use a band pass filter and to set the lower limit to zero because that implies an effort to filter negative frequencies that do not exist. It is not known exactly why the band pass filter (adjusted as noted) achieves superior results at very low frequencies; however, laboratory experiments by the inventor confirm that the use of a band pass filter does permit accurate and effective automatic processing of the resulting signal, which is otherwise unreliable.

It should be noted that while the nausea monitoring arrangement according to the invention has been depicted in FIG. 1 of the drawing as a combination of discrete functional units, the invention is capable of being implemented in the form of an appropriate programmed general purpose computer, in which case, the sensors 1, amplifier 2, analog low pass filter 3 and analog to digital converter 4 are separate peripheral units, with the remainder of the functions indicated in FIG. 1 being performed by the computer itself.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. Method of processing analog signals indicative of detected myoelectrical activity, said method comprising the steps of:
    digitizing said analog signals to generate digital signals corresponding to said analog signals;
    filtering said digital signals via a digital band pass filter having a lower limit of a pass band thereof set at approximately zero cpm;
    comparing filtered digital signals from said digital band pass filter with at least a predetermined signal pattern indicative of a preselected physiological activity;
    providing a human readable signal in response to detection of a match between said filtered digital signals and said at least a predetermined signal patterns.

2. Method according to claim 1 wherein said lower limit of said pass band of said digital band pass filter falls within a range of from 0.0 to 1.0 cpm.

3. Method according to claim 1 wherein said pass band filter has an upper limit set at a frequency of approximately 15 cpm.

4. Method according to claim 1 wherein said comparing step is performed in a digital computer having said at least a predetermined signal pattern stored in a memory thereof.

5. Method according to claim 1 wherein said comparing step is performed manually by observation of a visual display unit coupled to receive said filtered digital signals.

6. Method for near real time detection of an imminent onset of nausea, said method comprising the steps of:
    detecting analog signals generated by gastric myoelectric activity;
    digitizing said analog signals to generate digital signals corresponding to said analog signals;
    filtering said digital signals by means of a digital band pass filter having a pass band with a lower limit thereof set at approximately zero cpm;
    comparing filtered digital signals, by means of a digital computer, with predetermined signal patterns indicative of an onset of nausea;
    providing a human readable signal in response to detection of a match between said filtered digital signals and said predetermined signal patterns.

7. Method according to claim 6 wherein said lower limit of said pass band of said digital band pass filter falls within a frequency range of from 0.0 cpm to a frequency which is less than a lowest known frequency of said analog signals.

8. Method according to claim 6 wherein said lower limit of said pass bend of said digital band pass filter falls within a range of from 0.0 to 1.0 cpm.

9. Method according to claim 6 wherein said pass band has an upper limit set at a frequency of approximately 15 cpm.

10. Method for detection of onset of gastric dysrhythmias and imminent nausea, said method comprising the steps of:
    detecting analog signals generated by gastric myoelectrical activity;
    digitizing said analog signals;
    passing digitized signals generated in said digitizing step through a digital band pass filter having a pass band with a lower limit thereof set at approximately zero cpm;

comparing filtered digitized signals from said digital band pass filter with at least a predetermined stored signal pattern indicative of an onset of nausea.

11. Method according to claim 10 wherein said lower limit of said pass band of said digital band pass filter falls within a frequency range of from 0.0 cpm to a frequency which is less than a lowest known frequency of said analog signals.

12. Method according to claim 10 wherein said lower limit of said pass bend of said digital band pass filter falls within a range of from 0.0 to 1.0 cpm.

13. Method according to claim 10 wherein said comparing step is performed by observation of a visual display of said filtered digitized signals.

14. Method according to claim 10 wherein said comparing step is performed by means of a digital computer.

15. Method according to claim 10 wherein said pass band has an upper limit set at a frequency of approximately 15 cpm.

16. Apparatus for processing analog signals indicative of detected myoelectrical activity, said apparatus comprising:

an analog to digital converter coupled to receive said analog signals;

a digital band pass filter coupled to receive digital signals from said analog to digital converter said digital band pass filter having a pass band with a lower limit thereof set at approximately zero cpm;

means for comparing filtered digital signals with at least one predetermined signal pattern indicative of a preselected physiological activity;

a human readable signal device activated in response to detection of a match between said filtered digital signals with said at least one predetermined signal pattern.

17. Apparatus according to claim 16 wherein said lower limit of said pass bend of said digital band pass filter falls within a range of from 0.0 to 1.0 cpm.

18. Apparatus according to claim 16 wherein said pass band has an upper limit set at a frequency of approximately 15 cpm.

19. Apparatus according to claim 16 wherein said means for comparing comprises a digital computer having said at least one predetermined signal pattern stored in a memory thereof.

20. Apparatus for near real time detection of an onset of gastric dysrhythmia and imminent nausea, comprising:

electrodes for generating analog signals indicative of gastric myoelectrical activity;

an analog to digital converter coupled to receive said analog signals form said electrodes;

a digital band pass filter coupled to receive digital signals output by said analog to digital computer, said digital band filter having a lower limit of a pass band thereof adjusted to a frequency of approximately zero cpm;

a memory having stored therein at least a predetermined digital signal pattern indicative of an onset of nausea;

a digital computer for comparing filtered digital signals from said digital band pass filter with said at least a predetermined digital signal pattern; and an alarm signal activated by said digital computer in response to detection of a match between said filtered digital signals and said at least a predetermined digital signal pattern.

21. Apparatus according to claim 20 wherein said lower limit of said pass band of said digital band pass filter falls within a frequency range of from 0.0 cpm to a frequency which is less than a lowest known frequency of said analog signals.

22. Apparatus according to claim 20 wherein said lower limit of said pass bend of said digital band pass filter falls within a range of from 0.0 to 1.0 cpm.

23. Apparatus for detecting onset of imminent nausea, based upon analog electrical signals indicative of gastric myoelectrical activity, comprising:

an analog to digital converter coupled to receive said analog electrical signal;

a digital band pass filter coupled to receive digitized signals from said analog to digital converter, said band pass filter having a pass band with a lower limit set at a frequency of approximately zero cpm;

means for comparing filtered digital signals from said digital band pass filter with at least one predetermined signal pattern indicative of an onset of nausea.

24. Apparatus according to claim 23 wherein said lower limit of said pass band of said digital band pass filter falls within a frequency range of from 0.0 cpm to a frequency which is less than a lowest known frequency of said analog signals.

25. Apparatus according to claim 23 wherein said lower limit of said pass bend of said digital band pass filter falls within a range of from 0.0 to 1.0 cpm.

26. Apparatus according to claim 23 wherein said means for comparing comprises a digital computer having said at least one predetermined signal pattern stored in a memory thereof.

27. Apparatus according to claim 26 wherein said pass band has an upper limit set to a frequency of approximately 15 cpm.

* * * * *